United States Patent [19]

Hewelt

[11] Patent Number: 5,644,241

[45] Date of Patent: Jul. 1, 1997

[54] MEASUREMENT OF SOLID PARTICLE CONCENTRATION IN A FLUID STREAM RESPONSIVE TO MAGNITUDE AND RATE OF CHANGE OF A TRIBOELECTRIC PROBE OUTPUT SIGNAL

[75] Inventor: Scott M. Hewelt, China, Mich.

[73] Assignee: Bindicator Company, Port Huron, Mich.

[21] Appl. No.: 533,438

[22] Filed: Sep. 25, 1995

[51] Int. Cl.[6] .................................................. G01N 27/60
[52] U.S. Cl. ........................ 324/454; 324/71.1; 73/861.04
[58] Field of Search ..................................... 324/452, 454,
324/464, 71.1, 601; 73/28.02, 861.04

[56] References Cited

U.S. PATENT DOCUMENTS

| | | | |
|---|---|---|---|
| 3,359,796 | 12/1967 | Dimick et al. | 73/194 |
| 4,607,228 | 8/1986 | Reif | 324/454 |
| 4,619,145 | 10/1986 | Girgenti | 73/861.04 |
| 4,631,482 | 12/1986 | Newton et al. | 324/454 |
| 4,714,890 | 12/1987 | Dechene et al. | 324/454 |
| 4,904,944 | 2/1990 | Dechene et al. | 324/454 |
| 5,048,335 | 9/1991 | Marsh et al. | 73/304 |
| 5,054,325 | 10/1991 | Dechene et al. | 73/861.04 |
| 5,088,325 | 2/1992 | Eichberger et | 73/304 |
| 5,223,819 | 6/1993 | Marsh et al. | 340/617 |
| 5,287,061 | 2/1994 | Dechene et al. | 324/454 |
| 5,448,172 | 9/1995 | Dechene et al. | 324/454 |
| 5,541,518 | 7/1996 | Babbitt et al. | 324/454 |

*Primary Examiner*—Kenneth A. Wieder
*Assistant Examiner*—Diep Do
*Attorney, Agent, or Firm*—Barnes, Kisselle, Raisch, Choate, Whittemore & Hulbert

[57] ABSTRACT

Apparatus for measuring concentration of solid particles in a fluid stream that includes a probe for disposition in the fluid stream to provide an electrical probe signal as a triboelectric function of concentration of solid particles in the fluid stream. A first circuit is coupled to the probe for providing a first electrical signal as a proportional function of the probe signal. A second circuit is coupled to the probe for providing a second electrical signal as a function of rate of change of the probe signal. Differential amplifiers received the first and second signals, and provide a third signal as a function of a difference therebetween. An apparatus output signal is provided when such difference exceeds a preselected threshold.

12 Claims, 2 Drawing Sheets

MEASUREMENT OF SOLID PARTICLE CONCENTRATION IN A FLUID STREAM RESPONSIVE TO MAGNITUDE AND RATE OF CHANGE OF A TRIBOELECTRIC PROBE OUTPUT SIGNAL

The present invention is directed to a method and apparatus for measuring concentration of solid particles in a fluid stream such as air employing the so-called triboelectric effect.

BACKGROUND AND SUMMARY OF THE INVENTION

It has heretofore been proposed to measure concentration of solid materials, such as dust, powder or granular products, flowing in a pneumatic conveyor line. One typical installation would be downstream of a dust collector, with the device being configured to sense material in suspension and thus indicating failure at the dust collector. Another application is as a flow sensor to monitor continuous flow of material in a pneumatic conveyor, and to provide an indication of flow termination due, for example, to a plugged conveyor or loss of material feed. It is a general object of the present invention to provide a method and apparatus for measuring concentration of solid particles in a fluid stream employing the triboelectric effect that are of simple and inexpensive design, that do not require recalibration during operation, that automatically adjust for voltage and temperature drift during operation, that have operator selectable sensitivity, and that may be readily employed with minimum operator configuration as either a flow sensor or flow-interruption sensor.

Briefly stated, concentration of solid particles in a fluid stream is monitored in accordance with a presently preferred implementation of the invention by positioning a sensor or probe in the fluid stream so as to provide a sensor output signal that varies as a function of triboelectric effect of solid particles in the stream on the probe, and thus as a function of concentration of the particles in the fluid stream. In accordance with a distinguishing feature of the present invention, both magnitude and rate of change of the sensor signal are monitored, and an output signal is provided when both magnitude and rate of change of the sensor signal exceed a preselected threshold. By monitoring both magnitude and rate of change of the sensor signal, gradual changes due to voltage and temperature drift are ignored. This technique eliminates any requirement for a dead band to accommodate voltage drift, or for additional circuitry to adjust for temperature compensation. Following selection of desired sensitivity and installation of the apparatus, no further calibration is necessary. Inexpensive off-the-shelf electronic components can be utilized without batch testing for low offset voltage or temperature drift.

Apparatus for measuring concentration of solid particles in a fluid stream in accordance with the present invention thus includes a probe for disposition in the fluid stream to provide an electrical probe signal as a triboelectric function of concentration of solid particles in the fluid stream. A first circuit is coupled to the probe for providing a first electrical signal as a proportional function of magnitude of the probe signal. A second circuit is coupled to the probe for providing a second electrical signal as a function of rate of change of the probe signal. Differential amplifiers received the first and second signals, and provide a third signal as a function of a difference therebetween. An apparatus output signal is provided when such difference exceeds a preselected threshold. The first circuit in the preferred embodiment of the invention includes facility for adjusting sensitivity of the apparatus by selectively proportionately scaling the first signal to the probe signal. This sensitivity adjustment circuit comprises a switch-selectable voltage divider. The differential amplifier provides the third signal when either of the first and second signals exceeds the other by more than the preselected threshold. In this way, the apparatus is responsive to both positive and negative changes in concentration of solid particles in the fluid stream, and thus may be employed as either a flow sensor or a flow-interruption sensor. In this respect, the apparatus circuitry also includes facility for selectively delaying provision of the apparatus output signal, and fail-safe facility for providing the apparatus output signal independent of particle flow in the event of circuit or power failure.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figure 1:
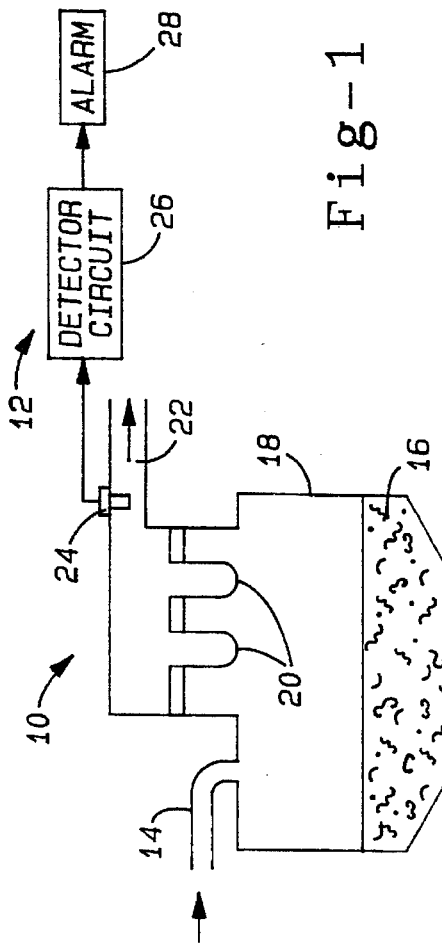
FIG. 1 is a schematic diagram of a dust collection system equipped with a flow sensor in accordance with the present invention.

FIG. 1 illustrates a dust collector system 10 equipped with a flow sensor 12 in accordance with the present invention. In system 10, an input pneumatic conveyor 14 feeds material 16 such as grain to a hopper 18. Grain 16 collects in the lower portion of hopper 18 for output to a railway car, for example. Filter bags 20 are disposed at the upper portion of hopper 18, and air is drawn through filter bags 20 to a pneumatic conveyor output 22. The purpose of sensor 12 in this application is to detect presence of dust or other particles in pneumatic output line 22, and thus to detect rupture or failure at one or both of the filter bags 20. Flow sensor 12 includes a triboelectric probe or sensor 24 disposed within pneumatic line 22. Probe 24 provides an electrical probe or sensor signal to a detector circuit 26 that varies, according to the so-called triboelectric effect, with concentration of particles in the fluid stream passing the probe. That is, electric charge carried by particles in the air stream transfer to the probe, and the amplitude of the probe output signal is thus a direct function of concentration of particles in the air stream. Detector circuit 26 is responsive to such probe signal to provide an output signal to an alarm 28 when concentration of particles in the air stream exceeds a preselected threshold, thus indicating failure at one or more of the filter bags 20.

Figure 2:
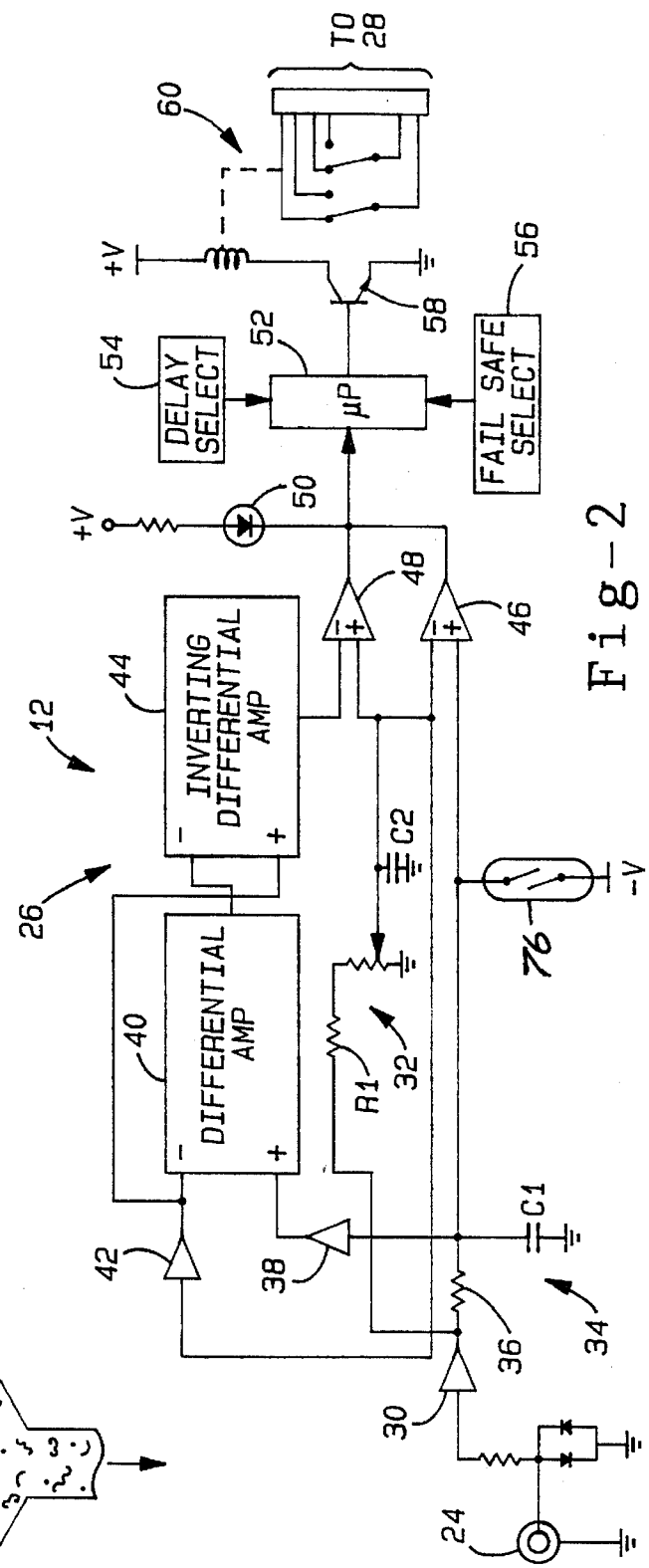
FIG. 2 is a functional block diagram of the flow sensor illustrated in FIG. 1.

Sensor circuit 12 is illustrated in greater detail in FIG. 2 as including a high-gain high-impedance input amplifier 30 that receives the signal from probe 24. The output of amplifier 30 is fed to an adjustable voltage divider circuit 32 for selecting sensitivity of the overall detector circuit 26. The output of amplifier 30 is also fed to a delay circuit 34 that includes a resistor 36 connected in series with a capacitor C1. The voltage across capacitor C1, as compared with the voltage across capacitor C2, thus varies as a function of rate of change of the signal from probe 24 and amplifier 30.

The voltage across capacitor C1 is connected through a unity gain amplifier 38 to one input of a differential amplifier circuit 40. The other input to differential amplifier circuit 40 is received from sensitivity adjustment circuit 32 across a capacitor C2, and through a second unity gain amplifier 42. The output of differential amplifier circuit 40, which varies as a function of the voltage $V_{C1}$ across capacitor C1 minus the voltage $V_{C2}$ across capacitor C2, is fed to an inverting differential amplifier circuit 44, which provides an output that varies as a function of the quantity $(2V_{C2}-V_{C1})$.

A first comparator 46 receives a signal input from capacitor C1 and a reference input from capacitor C2, and thus provides an output that switches high and low as a function of a comparison between the voltages $V_{C1}$ and $V_{C2}$. A second comparator 48 receives a reference input from capacitor C2 and a signal input from inverting differential amplifier 44. Comparator 48 thus provides an output that switches high and low as a function of a comparison between the quantity $(2V_{C2}-V_{C1})$ and voltage $V_{C2}$. The output of comparator 46 thus responds to an increase in output voltage from amplifier 30, while the output of comparator 48 responds to a decrease in such output voltage. At the same time, both comparators 46, 48 are responsive to the rate of change of the output of amplifier 30 by means of the delay circuit consisting of resistor 36 and capacitor C1. Thus, when both the magnitude and rate of change of the probe signal amplifier output exceed the threshold settings of one of the comparators 46, 48 in cooperation with sensitivity adjustment circuit 32, the output of one of the comparators 46, 48 switches low, illuminating an LED 50 and providing an input alarm signal to a microprocessor 52. Microprocessor 52 also receives inputs from delay and fall safe selection circuits 54, 56, and provides a detector circuit output to alarm 28 (FIG. 1) through an output transistor 58 and an output relay 60.

Figure 3:
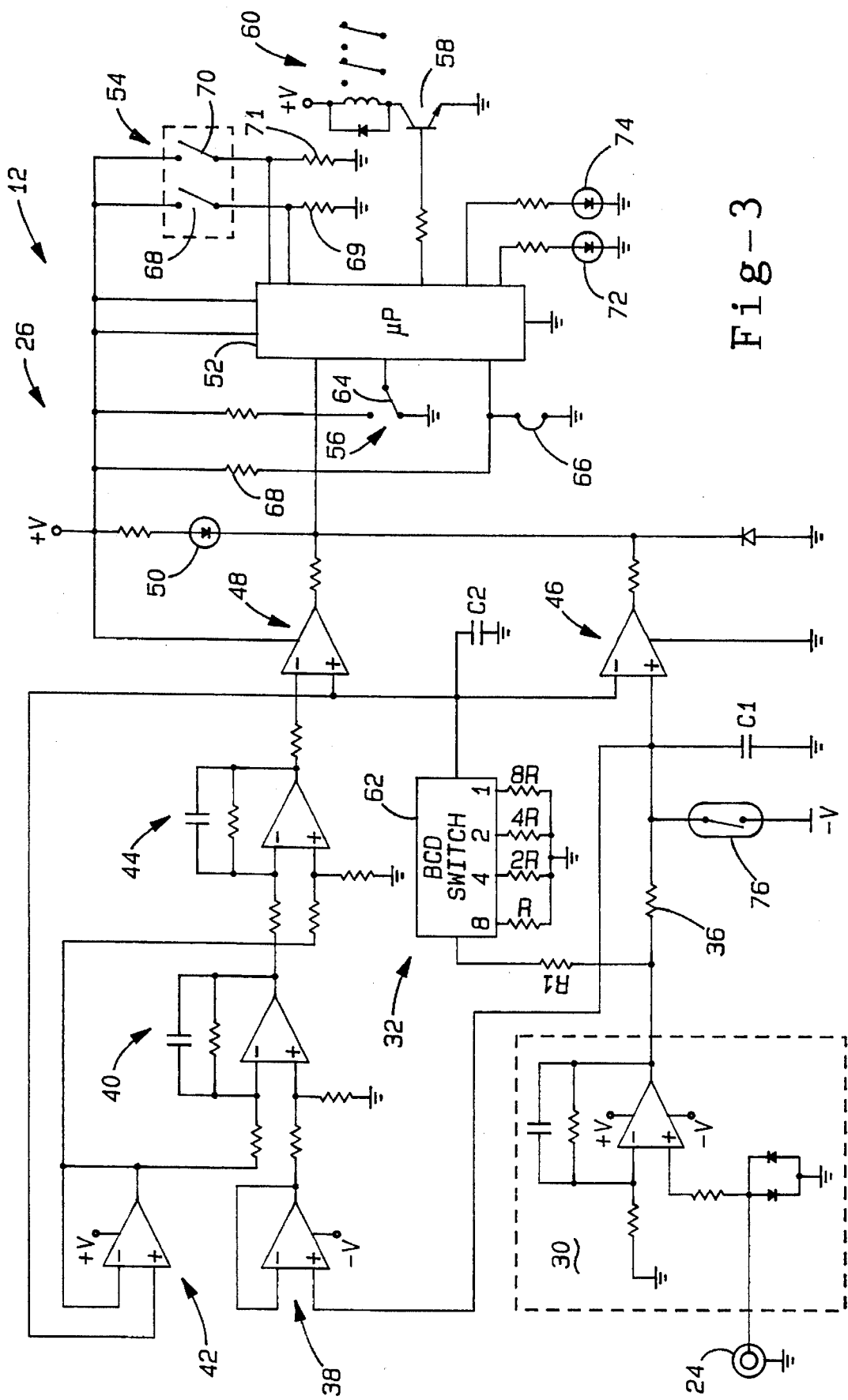
FIG. 3 is an electrical schematic diagram of the flow sensor illustrated functionally in FIG. 2.

FIG. 3 illustrates detector circuit 26 in greater detail. Sensitivity selection circuit 32 includes a BCD switch 62 for selectively configuring the voltage divider that consists of the resistor R1 coupled to probe amplifier 30, and the resistors R, 2R, 4R and 8R. Thus, the voltage appearing across capacitor C2 is proportionately related to the voltage output of amplifier 30 as a function of operator setting of switch 62. Fall safe selection circuit 56 comprises a switch 64 that provides either a high or low voltage input to a corresponding port of microprocessor 52. The setting of switch 64 is selected as a function of the output desired at relay 60 in the event of circuit or power failure. For example, when detector circuit 26 is configured to provide an alarm output upon detection of dust in what should otherwise be a clear fluid stream, as in broken bag detection configuration 10 illustrated in FIG. 1, switch 64 may be configured to connect the corresponding microprocessor port to electrical ground as illustrated in FIG. 3. Microprocessor 52 is suitably programmed to respond to this input signal so that transistor 58 and relay 60 are normally energized, and become deenergized in the event of detection of material at probe 24. Thus, in the event of either circuit or power failure, relay 26 becomes deenergized, and thus provides the desired alarm signal independent of actual conditions at probe 24.

A further input port of microprocessor 52 is connected to electrical ground through a removable jumper or switch 66, and to the voltage supply through a pull-up resistor 68. Jumper 66 is provided to configure detector circuit 26 to be responsive either to presence of particles in a normally clear fluid stream (FIG. 1) with jumper 66 in place, or for detection of disappearance of particulate matter from an otherwise continuous flow with jumper 66 removed. Delay selection circuit 54 comprises a pair of switches 68, 70 and associated series resistors 69, 71 connected to corresponding microprocessor input ports for selecting one of four delay settings by which activation or de activation of relay 60 is delayed as compared with the outputs of comparators 46, 48 to accommodate transient changes in material flow. Also connected to corresponding output ports of microprocessor 52 are a pair of LED's 72, 74. LED 72 is green, and indicates application of electrical power to the apparatus. LED 74 is red, and indicates an alarm status when illuminated. Both LED's are visible through the unit housing. See U.S. Pat. No. 5,223,819, assigned to the assignee hereof. A reed switch 76 is connected across capacitor C1, and is responsive to imposition of a magnetic field from outside of the apparatus housing for selectively testing circuit operation. Such external test feature is described in greater detail in U.S. Pat. No. 5,048,335.

In operation, microprocessor 52 contains internal programming to respond to a low input from comparators 46, 48, after a delay set by switches 54, to change the status of transistor 58 and relay 60. In the example discussed above in which transistor 58 and output relay 60 are normally energized, a low output at comparator 46, indicating detection of dust at sensor 24, turns transistor 58 and relay 60 off after the delay set by switches 54. Of course, if the output of comparator 48 is only transient and disappears during the delay time, transistor 58 and relay 60 remain energized.

There is thus provided in accordance with the present invention a method and apparatus for measuring concentration of solid particles in a fluid stream that satisfy all of the objects and aims previously set forth. By monitoring both magnitude and rate of change of the sensor output, there is no need for either continuous calibration or a voltage dead band to accommodate either voltage or temperature drift. Nor is there any need for continuous circuit calibration. The method and apparatus of the present invention are simple and inexpensive to implement, and automatically adjust for voltage and temperature drift. The disclosed embodiments provide for operator selection of circuit sensitivity, to be set for example upon initial installation in a fluid flow system. Furthermore, the disclosed circuit embodiments may be employed either as a flow sensor for detecting presence of particles in a normally clear air stream, or as a flow interruption sensor for detecting absence of particles in a particulate conveyor environment.

I claim:

1. Apparatus for measuring concentration of solid particles in a fluid stream that comprises:

triboelectric probe means for disposition in the fluid stream to provide an electrical probe signal as a function of concentration of solid particles in the fluid stream, first circuit means coupled to said probe means for providing a first electrical signal as a proportionate function of magnitude of said probe signal, second circuit means for providing a second electrical signal as a function of rate of change of said probe signal, third circuit means for receiving said first and second signals, and providing a third signal as a function of a difference therebetween, and means for providing an output signal when said difference exceeds a preselected threshold.

2. The apparatus set forth in claim 1 wherein said first circuit means includes means for adjusting sensitivity of said apparatus by selectively proportionately scaling said first signal to said probe signal.

3. The apparatus set forth in claim 2 wherein said sensitivity adjusting means comprises voltage divider means and switch means for selectively connecting said voltage divider means in said first circuit means.

4. The apparatus set forth in claim 1 wherein said third circuit means includes means providing said third signal when either of said first and second signals exceeds the other by said preselected threshold, such that said apparatus is responsive to both positive and negative changes in concentration of solid particles in the fluid stream.

5. The apparatus set forth in claim 4 further comprising means for selectively delaying said output signal to accommodate transient changes in particle concentration at said probe means.

6. The apparatus set forth in claim 1 wherein said means for providing said output signal includes fail-safe circuit means for providing said output signal independent of said first and second signals in the event of circuit as power failure at said apparatus.

7. A method of monitoring concentration of solid particles in a fluid stream that comprises the steps of:

(a) positioning a sensor in the fluid stream so as to provide a sensor signal as a function of triboelectric effect of particles in the stream, (b) monitoring both magnitude and rate of change of such sensor signal, and (c) providing an output signal when both magnitude and rate of change of said sensor signal exceed a preselected threshold.

8. Apparatus for measuring a condition of materials that comprises:

probe means for providing an electrical probe signal as a function of material condition, first circuit means coupled to said probe means for providing a first electrical signal as a proportionate function of magnitude of said probe signal, second circuit means for providing a second electrical signal as a function of rate of change of said probe signal, third circuit means for receiving said first and second signals, and providing a third signal as a function of a difference therebetween, and means for providing an output signal when said difference exceeds a preselected threshold.

9. The apparatus set forth in claim 8 wherein said first circuit means includes means for adjusting sensitivity of said apparatus by selectively proportionately scaling said first signal to said probe signal.

10. The apparatus set forth in claim 9 wherein said sensitivity adjusting means comprises voltage divider means and switch means for selectively connecting said voltage divider means in said first circuit means.

11. The apparatus set forth in claim 8 wherein said third circuit means includes means providing said third signal when either of said first and second signals exceeds the other by said preselected threshold, such that said apparatus is responsive to both positive and negative changes in material condition.

12. The apparatus as set forth in claim 11 wherein said probe means comprises a triboelectric probe for providing said probe signal as a function of concentration of solid particles in a fluid stream.

* * * * *